United States Patent
Sun et al.

(10) Patent No.: US 10,159,722 B2
(45) Date of Patent: Dec. 25, 2018

(54) ENZYME-ACTIVATED COLLAGEN AND TISSUE MATRICES

(71) Applicant: LifeCell Corporation, Branchburg, NJ (US)

(72) Inventors: Wenquan Sun, Warrington, PA (US); Xiaohua Yu, Willimantic, CT (US)

(73) Assignee: LifeCell Corporation, Madison, NJ (US)

( * ) Notice: Subject to any disclaimer, the term of this patent is extended or adjusted under 35 U.S.C. 154(b) by 167 days.

(21) Appl. No.: 15/254,629

(22) Filed: Sep. 1, 2016

(65) Prior Publication Data

US 2017/0065743 A1 Mar. 9, 2017

Related U.S. Application Data

(63) Continuation of application No. 13/777,153, filed on Feb. 26, 2013, now Pat. No. 9,592,278.

(60) Provisional application No. 61/608,458, filed on Mar. 8, 2012.

(51) Int. Cl.
| | |
|---|---|
| *A61K 38/54* | (2006.01) |
| *A61K 38/48* | (2006.01) |
| *A61L 27/36* | (2006.01) |
| *A61L 27/24* | (2006.01) |
| *A61L 27/54* | (2006.01) |

(52) U.S. Cl.
CPC .......... *A61K 38/4886* (2013.01); *A61L 27/24* (2013.01); *A61L 27/362* (2013.01); *A61L 27/3604* (2013.01); *A61L 27/3687* (2013.01); *A61L 27/54* (2013.01); *A61L 2300/254* (2013.01)

(58) Field of Classification Search
CPC . A61K 38/4886; A61L 27/24; A61L 27/3604; A61L 27/362; A61L 27/3687
See application file for complete search history.

(56) References Cited

U.S. PATENT DOCUMENTS

| | | |
|---|---|---|
| 4,233,969 A | 11/1980 | Lock et al. |
| 4,373,519 A | 2/1983 | Errede et al. |
| 4,569,348 A | 2/1986 | Hasslinger |
| 4,703,108 A | 10/1987 | Silver et al. |
| 5,149,331 A | 9/1992 | Ferdman et al. |
| 5,263,971 A | 11/1993 | Hirshowitz et al. |
| 5,298,015 A | 3/1994 | Komatsuzaki et al. |
| 5,336,616 A | 8/1994 | Livesey et al. |
| 5,364,756 A | 11/1994 | Livesey et al. |

(Continued)

FOREIGN PATENT DOCUMENTS

| | | |
|---|---|---|
| WO | WO-90/00060 A1 | 1/1990 |
| WO | WO-2002/40630 A2 | 5/2002 |

(Continued)

OTHER PUBLICATIONS

Duarte et al., "Bacterial collagenases—A review", Critical Reviews in Microbiology, vol. 42, No. 1, pp. 106-126 (2016).

(Continued)

*Primary Examiner* — Kara D Johnson
(74) *Attorney, Agent, or Firm* — McCarter & English, LLP

(57) ABSTRACT

Devices and methods for treating defects in connective tissue are provided along with methods for making such devices. The devices can include enzyme-activated acellular tissue matrices that facilitate regrowth of the damaged tissue.

20 Claims, 10 Drawing Sheets

Specification includes a Sequence Listing.

(56) References Cited

U.S. PATENT DOCUMENTS

| | | | |
|---|---|---|---|
| 5,437,651 | A | 8/1995 | Todd et al. |
| 5,549,584 | A | 8/1996 | Gross |
| 5,636,643 | A | 6/1997 | Argenta et al. |
| 5,645,081 | A | 7/1997 | Argenta et al. |
| 5,993,844 | A | 11/1999 | Abraham et al. |
| 6,071,267 | A | 6/2000 | Zamierowski |
| 6,135,116 | A | 10/2000 | Vogel et al. |
| 6,345,623 | B1 | 2/2002 | Heaton et al. |
| 6,381,026 | B1 | 4/2002 | Schiff et al. |
| 6,553,998 | B2 | 4/2003 | Heaton et al. |
| 6,814,079 | B2 | 11/2004 | Heaton et al. |
| 6,933,326 | B1 | 8/2005 | Griffey et al. |
| 7,198,046 | B1 | 4/2007 | Argenta et al. |
| 7,358,284 | B2 | 4/2008 | Griffey et al. |
| 7,498,040 | B2 | 3/2009 | Masinaei et al. |
| 7,498,041 | B2 | 3/2009 | Masinaei et al. |
| 2002/0120185 | A1 | 8/2002 | Johnson |
| 2003/0035843 | A1 | 2/2003 | Livesey et al. |
| 2003/0087428 | A1* | 5/2003 | Wolfinbarger, Jr. ... A61K 35/32 435/325 |
| 2003/0143207 | A1 | 7/2003 | Livesey et al. |
| 2005/0013870 | A1 | 1/2005 | Freyman et al. |
| 2005/0028228 | A1 | 2/2005 | McQuillan et al. |
| 2005/0043819 | A1 | 2/2005 | Schmidt et al. |
| 2005/0159822 | A1 | 7/2005 | Griffey et al. |
| 2006/0073592 | A1 | 4/2006 | Sun et al. |
| 2006/0127375 | A1 | 6/2006 | Livesey et al. |
| 2006/0210960 | A1 | 9/2006 | Livesey et al. |
| 2007/0009586 | A1 | 1/2007 | Cohen et al. |
| 2007/0219471 | A1 | 9/2007 | Johnson et al. |
| 2007/0248575 | A1 | 10/2007 | Connor et al. |
| 2008/0027542 | A1 | 1/2008 | McQuillan et al. |
| 2008/0027562 | A1 | 1/2008 | Fujisato et al. |
| 2009/0035289 | A1 | 2/2009 | Wagner et al. |
| 2009/0130221 | A1 | 5/2009 | Bolland et al. |
| 2009/0306790 | A1 | 12/2009 | Sun |
| 2010/0040687 | A1 | 2/2010 | Pedrozo et al. |

FOREIGN PATENT DOCUMENTS

| | | | |
|---|---|---|---|
| WO | WO-2007/043513 A1 | 4/2007 | |
| WO | WO 2009149224 A2 * | 12/2009 | ......... A61L 27/3687 |

OTHER PUBLICATIONS

Jung et al., "Identification of metal ligands in the Clostridium histolyticum ColH collagenase", Journal of Bacteriology, vol. 181, No. 9, pp. 2816-2822 (May 1999).
Argenta, L.C. et al., "Vacuum-Assisted Closure: A New Method for Wound Control and Treatment: Clinical Experience," *Annals of Plastic Surgery*, 38(6):563-577 (Jun. 1997).
Bellon et al. (2004) "Matrix metalloproteinases and matrikines in angiogenesis", Critical Reviews in Oncology/Hematology 49, 203-220.
Blackburn II, J.H. et al., "Negative-Pressure Dressings as a Bolster for Skin Grafts," *Annals of Plastic Surgery*, 40(5):453-457 (May 1998).
Brandi, C., et al., "Treatment with vacuum-assisted closure and cryo-preserved homologous (de-epidermalised dermis of complex traumas to the lower limbs with loss of substance, and bones and tendons exposure," *Journal of Plastic, Reconstructive and Aesthetic Surgery*, 61(12):1507-1511 (2008).
Chariker, M.E. et al., "Effective management of incisional and cutaneous fistulae with closed suction wound drainage," *Contemporary Surgery*. 34:59-63 (Jun. 1989).
Chinn, S.D. et al., "Closed Wound Suction Drainage," *The Journal of Foot Surgery*, 24(1):76-81 (1985).
D.Attilo Jr., P.P. et al., "Medical Textiles: Application of an Absorbable Barbed Bi-directional Surgical Suture," *Journal of Textile and Apparel, Technology and Management*, 2(2):1-5 (Spring 2002).
Dagalakis, N. et al., "Design of an artificial skin. Part III. Control of pore structure," *J. Biomed. Mater. Res.*, 14:511-528 (1980).
Defranzo, A.J. et aL., "Vacuum-Assisted Closure for the Treatment of Abdominal Wounds," *Clinics in Plastic Surgery*, 33(2}:213-224 (Apr. 2086).
Dobrin, P.B. et al., "Elastase, collagenase, and the biaxial elastic properties of dog carotid artery," *Am. J. PhysioL Heart Circ. Physiol.*, 247:H124-H131 (1984).
Examination Report issued by the European Patent Office in European Patent Application No. 11153969.8, dated Apr. 9, 2013 (5 pages).
Flack, S. et al., "An economic evaluation of VAC therapy compared with wound dressings in the treatment of diabetic foot ulcers," *J. Wound Care*, 17(2):71-78 (Feb. 2008).
Griffey, S. et al., "Particulate Dermal Matrix as an Injectable Soft Tissue Replacement Material," *J. Biomed. Mater. Res. {Appl. Biomater,}*, 58:10-15 (2001).
Ju, Y.M. et al., "Beneficial Effect of Hydrophilized Porous Polymer Scaffolds in Tissue-Engineered Cartilage Formation," *J. Biomed. Mater. Res. Part B: Appl. Biomater.*, 85B:252-260 (2008; online Oct. 31, 2007).
Karlinsky. J.B. et al., "In Vitro Effects of Elastase and Collagenase on Mechanical Properties of Hamster Lungs," *Chest*, 69(2):275-276 (1976).
KCI Licensing, Inc., "V.A.C.® Therapy Safety Information," 2007, pp. 1-4.
Lu, G. et al., "Novel Porous Aortic Elastin and Collagen Scaffolds for Tissue Engineering," *Biomaterials*, 25(22):5227-5237 (2004).
Maquart, F. X. et al., "Matrikines in the regulation of extracellular matrix degradation," BIOCHIMIE, Mar. 1, 2005, vol. 87, No. 3-4, p. 353-360.
Masters, J., "Reliable, inexpensive and Simple Suction Dressings," Letters to the Editor, *British Journal of Plastic Surgery*, 51(3):267 (1998).
O'Brien et al., "The effect of pore size on cell adhesion in collagen-GAG scaffolds," *Biomaterials*, 26:433-441 (2005).
O'Connor, J. et al., "Vacuum-Assisted Closure for the Treatment of Complex Chest Wounds," *Ann. Thorac Surg.*, 79:1196-1200 (2005).
Randall, K.L, et al., "Use of an Acellular Regenerative Tissue Matrix in Combination with Vacuum-assisted Closure Therapy for Treatment of a Diabetic Foot Wound," *The Journal of Foot & Ankle Surgery*, 47(5):430-433 (2008).
Reihsner, R. et al., "Biomechanical properties of elastase treated palmar aponeuroses," *Connective Tissue Research*, 26:77-86 (1991).
Tedder, M.E. et al., "Stabilized Collagen Scaffolds for Heart Valve Tissue Engineering," *Tissue Engineering: Part A*, 00(00): 1-12 (2008).
Wei,H.J. et al., "Construction of varying porous structures in acellular bovine pericardia as a tissue-engineering extracellular matrix," *Biomaterials*, 26(14):1905-1913 (2005).
Wu, Z. et al., "Preparation of collagen-based materials for wound dressing," *Chinese Medical Journal*, 116(3):419-423 (2003).
Yang et al., "A cartilage EGM-derived 3-D porous acellular matrix scaffold for in vivo cartilage tissue engineering with PKH26-labeled chondrogenic bone marrow-derived mesenchymal stem cells," Biomaterials, 29(15): 2378-2387 (2008.
Yuan, H. et al., "Effects of collagenase and elastase on the mechanical properties of lung tissue strips," *J. App Physiol.*, 89:3-14 (2000).

* cited by examiner

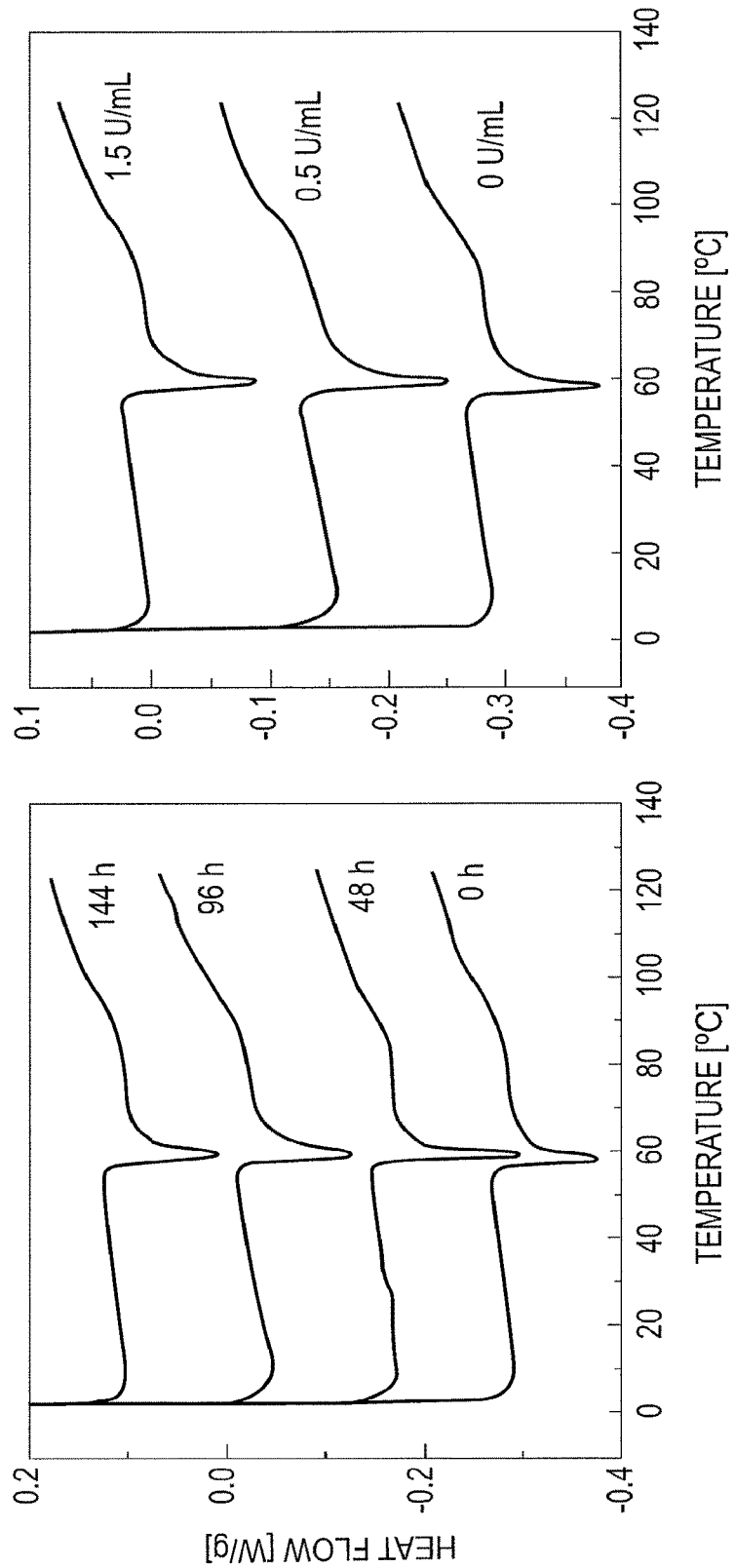

SEQUENCE LISTING

```
<160> NUMBER OF SEQ ID NOS: 6

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly His Lys
1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asn Tyr Tyr Ser Asn Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Gly Pro Val Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Gly Val Ala Pro Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Gly His Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued

```
          peptide

<400> SEQUENCE: 6

Asp Gly Gly Arg Tyr Tyr
1               5
```

US 10,159,722 B2

ENZYME-ACTIVATED COLLAGEN AND TISSUE MATRICES

This application is a continuation of U.S. application Ser. No. 13/777,153, filed on Feb. 26, 2013, which claims priority under 35 U.S.C. § 119 to U.S. Provisional Application No. 61/608,458, which was filed on Mar. 8, 2012.

SEQUENCE LISTING

The instant application contains a Sequence Listing which has been submitted electronically in ASCII format and is hereby incorporated by reference in its entirety. Said ASCII copy, created on Jan. 16, 2015, is named 123436-09201_SL.txt and is 1,460 bytes in size.

The present disclosure relates to tissue matrices, and more particularly, to methods of preparing enzyme-activated tissue matrices and tissue matrices prepared according to those methods.

Matrikines are peptides released by proteolytic cleavage of tissue extracellular matrices. These bioactive peptides of collagen, elastin, decorin, laminine, fibronectin, and other matrix proteins may constitute chemical signals for surrounding cells. Matrikines are known to regulate cell activities in a manner similar to cytokines and growth factors. The roles of matrikines include the regulation of chemotaxis, mitogenesis, angiogenesis, and other processes.

Matrix metalloproteinases (MMPs) are enzymes known to cleave extracellular tissue matrices, resulting in the release of matrikines. The present invention discloses a method of deactivating MMPs and incorporating them into tissue matrices. The deactivated MMPs can be automatically re-activated upon implantation into animal or human patients, resulting in the release of matrikines. Such enzyme-activated tissue matrices may be useful in facilitating active healing, tissue integration, and tissue regeneration.

According to certain embodiments, a method for preparing a tissue matrix composition is provided. The method comprises selecting a collagen-based tissue matrix, and contacting the matrix with a composition containing an enzyme, wherein the composition containing an enzyme further contains a deactivating agent for reducing the activity of the enzyme.

In certain embodiments, a tissue matrix composition is provided. The composition comprises a collagen-based tissue matrix, wherein the matrix has been contacted with a composition containing an enzyme, and wherein the composition containing the enzyme further contains a deactivating agent for reducing the activity of the enzyme.

In certain embodiments, a method of treatment is provided. The method comprises selecting an anatomical site for treatment, selecting a collagen-based tissue matrix, wherein the matrix has been contacted with a composition containing an enzyme, and wherein the composition containing the enzyme further contains a deactivating agent for reducing the activity of said enzyme.

DESCRIPTION OF THE DRAWINGS

FIGS. 9A and 9B are charts showing the effect of MMP-1 treatment on pADM thermal stability as a function of time and MMP-1 concentration respectively, according to certain embodiments and described in Example 8.

DESCRIPTION OF CERTAIN EXEMPLARY EMBODIMENTS

Figure 1:
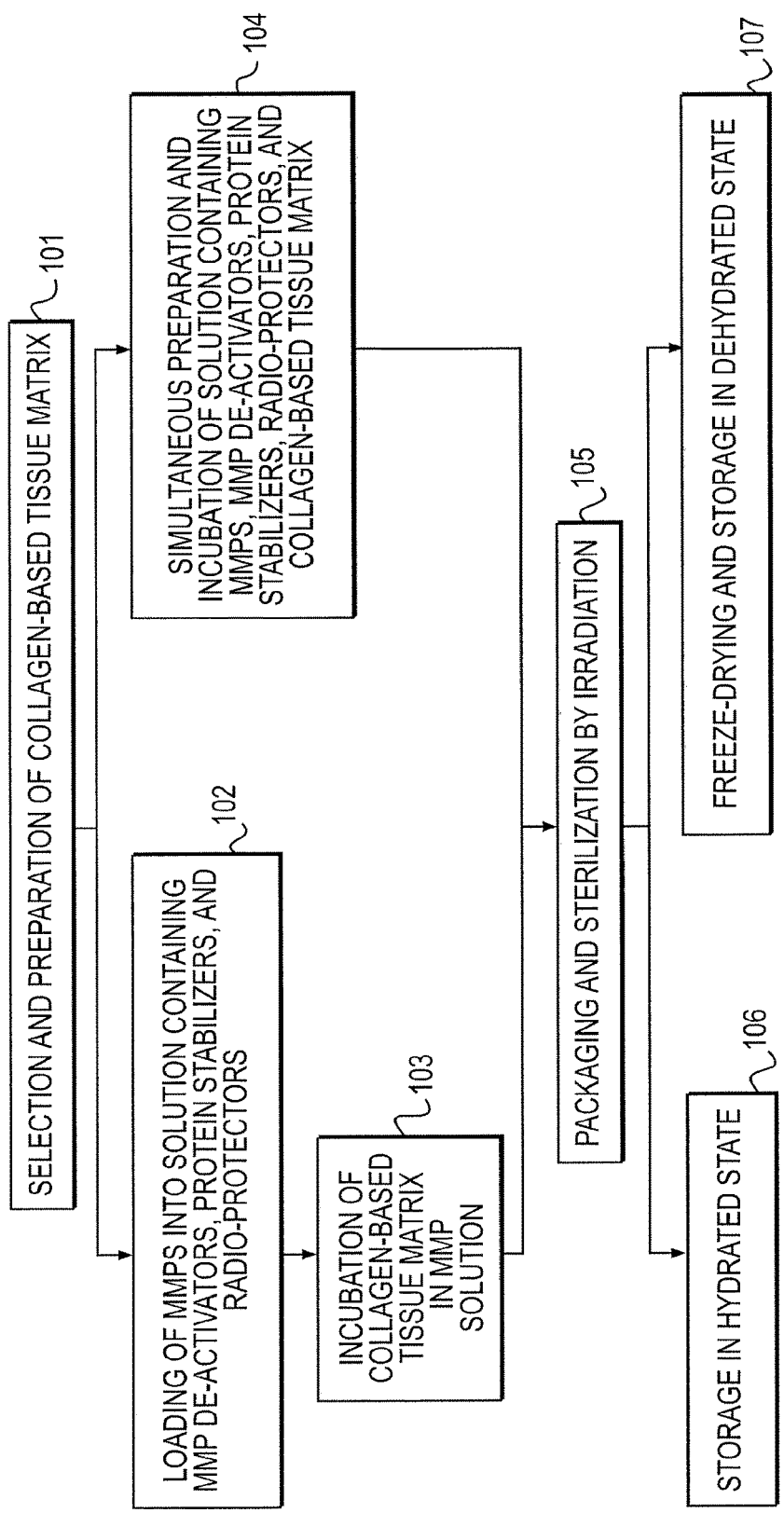
FIG. 1 is a flowchart summarizing the various steps that may be used to produce tissue matrices of the present disclosure, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, "tissue matrix" will refer to material derived from animal tissue that includes a collagen-containing matrix. Such tissue matrices can include intact tissues, tissues that have been partially or completely decellularized, or synthetic collagenous matrices (e.g., 3-D matrices formed from suspended or otherwise processed tissues). As described further below, suitable tissue matrices can be acellular. Any suitable tissue matrix can be used, depending on the intended implantation site, so long as the tissue is amenable for use with the methods described herein.

The enzyme-activated tissue matrix disclosed herein possesses several properties that make it suitable for use in tissue treatment. The tissue matrix is regenerative, permitting host cell repopulation and revascularization. The addition of matrix metalloproteinases (MMPs) to the tissue matrix further enhances active healing.

MMPs are metal-ion dependent enzymes that are able to degrade extracellular matrix proteins. MMPs include collagenases, gelatinases, stromelysins, matrilysins, membrane-type MMPs, and other types of MMPs. The degradation of the extracellular matrix by MMPs releases matrix-derived bioactive molecules. Through the release of these bioactive molecules, MMPs can modulate cellular and physiological processes, including morphogenesis, angiogenesis, and tissue repair.

MMP-mediated degradation of the extracellular matrix results in the liberation of matrikines, bioactive peptides with the ability to regulate cellular activity. Matrikines are known to modulate aspects of cellular activity, including cell proliferation, adhesion, migration, and apoptosis. Matrikines have also been implicated in protein synthesis and degradation. GHK (glycine-histidine-lysine tripeptide) (SEQ ID NO: 1), for example, is a collagen-derived matrikine that has been found to influence collagen synthesis, cell proliferation, and tissue repair. In addition to collagen, protein sources of matrikines include, for example, elastin and connective tissue glycoproteins.

In various embodiments of the present disclosure, MMPs are loaded into a tissue matrix to create a tissue matrix composition with enhanced capabilities for tissue regeneration. A deactivating agent is used to inhibit MMP activity until the tissue matrix composition is placed into the body, impeding degradation of extracellular matrix proteins until the appropriate time. Once placed inside the body, the MMPs are automatically reactivated, resulting in the release of matrikines and the subsequent enhancement of the healing process. In short, by incorporating specific matrix-degrading enzymes into tissue matrices, one can affect matrix degradation kinetics to facilitate active healing, tissue integration, and tissue regeneration.

According to certain embodiments, a method for preparing a tissue matrix composition is provided. The method comprises selecting a collagen-based tissue matrix, and contacting the matrix with a composition containing an enzyme, wherein the composition containing an enzyme further contains a deactivating agent for reducing the activity of the enzyme. In certain embodiments, a tissue matrix composition is provided. The composition comprises a collagen-based tissue matrix, wherein the matrix has been contacted with a composition containing an enzyme, and wherein the composition for containing an enzyme further contains a deactivating agent for reducing the activity of the enzyme. In certain embodiments, a method of treatment is provided. The method comprises selecting an anatomical site for treatment, selecting a collagen-based tissue matrix, wherein the matrix has been contacted with a composition containing an enzyme, and wherein the composition containing an enzyme further contains a deactivating agent for deactivating the activity of the enzyme.

A sample protocol in accordance with the disclosed methods is provided in FIG. 1. The order of certain steps can be changed as needed. Certain steps may also be added as necessary, while other steps may be omitted. Specific details regarding each step are provided throughout the present disclosure. A collagen-based tissue matrix is procured from a suitable source 101. A solution is prepared containing the desired MMPs and the appropriate MMP deactivators 102. Protein stabilizers and radio-protectors may also be incorporated into the solution. The collagen-based matrix is then incubated in the MMP solution to allow incorporation of the MMPs into matrix 103. In this instance, the MMPs have been deactivated prior to incorporation into the matrix. Alternatively, the MMPs, MMP-deactivating agent, and collagen-based matrix can be added simultaneously to a solution and allowed to incubate 104. After either method, the matrix, now loaded with deactivated MMPs, is subsequently packaged and sterilized by irradiation 105. Packaging the matrix prior to sterilization reduces handling and maintains sterility after sterilization. The sterilized package is then stored until implantation. The matrix can be stored in a hydrated state, i.e., in a suitable amount of the appropriate buffer 106. In the alternative, the matrix can also be stored in a dried, i.e., lyophilized state until further use 107. In either state, the matrix is adequately stored until implantation into a human or animal subject. Upon implantation, the deactivated MMPs in the matrices will be automatically reactivated by metal ions present within the subject, resulting in the release of matrikines that facilitate tissue repair.

The methods described herein can be used to produce enzyme-activated tissue matrices using a variety of tissue types, so long as the tissue includes a collagen-containing matrix amenable for use with the methods described herein. Such matrices can include intact tissues, tissues that have been partially or completely decellularized, or synthetic collagenous matrices (e.g., 3-D matrices formed from suspended or otherwise processed tissues).

In various embodiments, the tissue matrix can be produced from a range of tissue types. For example, the tissue matrix can be derived from fascia, pericardial tissue, dura, umbilical tissue, placental tissue, cardiac valve tissue, ligaments, tendons, arterial tissue, venous tissue, neural connective tissue, urinary bladder tissue, ureter tissue, and intestinal tissue. In some embodiments, the tissue matrix comprises a dermal tissue matrix. In certain embodiments, the tissue matrix comprises porcine dermal matrix.

In certain embodiments, the tissues can include a mammalian soft tissue. For example, in certain embodiments, the tissue can include mammalian dermis. In certain embodiments, the dermis can be separated from the surrounding epidermis and/or other tissues, such as subcutaneous fat. In certain embodiments, the tissue sample can include small intestine submucosa. In certain embodiments, the tissue samples can include human or non-human sources. Exemplary, suitable non-human tissue sources include, but are not limited to, pigs, sheep, goats, rabbits, monkeys, and/or other non-human mammals.

In some embodiments, the collagen-based matrix comprises an acellular tissue matrix. In certain embodiments, the matrices can be completely decellularized to acellular tissue matrices for patient use. For example, various tissues, such as skin, intestine, bone, cartilage, nerve tissue (e.g., nerve fibers or dura), tendons, ligaments, or other tissues can be completely decellularized to produce tissue matrices useful for patients. Suitable processes for producing acellular tissue matrices are described herein.

While an acellular tissue matrix may be made from the same species as the acellular tissue matrix graft recipient, different species can also serve as tissue sources. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Generally, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X100™, sodium deoxycholate, polyoxyethylene (20) sorbitan mono-oleate, one or more agents to prevent cross-linking, one or more protease inhibitors, and/or one or more enzymes. In some embodiments, the decellularization solution comprises 0.1% to 10% (w/v) TRITON-X-100™. In other embodiments, the decellularization solution comprises 0.5% to 5% (w/v) TRITON-X-100™. In some embodiments, the decellularization solution comprises 1% TRITON-X-100™ in RPMI media with gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents, the decellularization solution comprises 0.1% to 10% sodium deoxycholate. In other embodiments, 2% sodium deoxycholate is added to the decellularization solution.

It would be understood that variations can be made in the protocol above and still be within the scope of the present invention. For example, other physiological buffers can be utilized so long as they do not impede the decellularization process. In some embodiments, suitable detergents can include, but are not limited to, SDS, sodium cholate, sodium deoxycholate, TRITON-X-100™, and NP40™. The selected detergents can be used at a range of concentrations, for example, from 0.1 to 10% (w/v), 0.5 to 2%, 1 to 2%, 0.1 to 2%, 0.5 to 5%, 0.5 to 10%, 0.1 to 2%, or any values within those ranges.

After the decellularization process, the tissue sample is washed thoroughly with saline. In some exemplary embodiments, e.g., when xenogenic material is used, the decellularized tissue is treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineetahnsulfonic acid), 20 mM $CaCl_2$ and 20 mM $MgCl_2$. In some embodiments, the DNase solution comprises 30 units/ml DNase. Optionally, an antibiotic solution (e.g., gentamicin) may be added to the DNase solution. In some embodiments, the solution comprises 50 μg/ml gentamicin. Any suitable buffer can be used as long as the buffer provides suitable DNase activity.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., *J. Biol. Chem.* 263:17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., *Infect. Immun.* 56:1730 (1988); R. M. Hamadeh et al., *J. Clin. Invest.* 89:1223 (1992).

Because non-primate animals (e.g., pigs) produce α-gal epitopes, xenotransplantation of collagen-containing material from these mammals into primates often results in rejection because of primate α-gal binding to these epitopes on the collagen-containing material. The binding results in the destruction of the collagen-containing material by complement fixation and by antibody dependent cell cytotoxicity. U. Galili et al., *Immunology Today* 14:480 (1993); M. Sanrin et al., *Proc. Natl. Acad. Sci. USA* 90:11391 (1993); H. Good et al., *Transplant. Proc.* 24:559 (1992); B. H. Collins et al., *J. Immunol.* 154:550 (1995). Furthermore, xenotransplantation results in major activation of the immune system to produce increased amounts of high affinity α-gal antibodies. Accordingly, in some embodiments, when animals that produce α-gal antibodies are used as a tissue source, the substantial elimination of α-gal epitopes from cells and from extracellular components of the collagen-containing material, and prevention of cellular α-gal epitope re-expression can diminish the immune response against the collagen-containing material associated with α-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with α-galactosidase enzyme to eliminate α-gal epitopes if present in the tissue. In some embodiments, the enzymatic treatment may comprise 50 to 500 U/L α-galactosidase prepared in a suitable buffer. In some embodiments, the tissue sample is treated with α-galactosidase at a concentration of 200 or 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used provided adequate removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals, see co-pending U.S. application Ser. No. 10/896, 594 and U.S. Pat. No. 6,166,288, the disclosures of which are herein incorporated by reference in their entirety.

After selection and preparation of the collagen-based tissue matrix, an enzyme is selected for incorporation into the matrix. In certain embodiments, the enzyme is a matrix metalloproteinase (MMP). Suitable classes of MMPs include collagenases, gelatinases, stromelysins, matrilysins, membrane-type MMPs, as well as other types of MMPs. Specific MMPs suitable for use with the present invention include, but are not limited to, MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23, MMP-24, MMP-25, MMP-26, MMP-27, and MMP-28. The particular MMP selected may depend on the matrikines desired upon degradation of extracellular matrix or the particular cellular process to be affected. In certain embodiments, the MMP comprises MMP-1, MMP-3, or MMP-9, which are collagenases, stromelysins, and gelatinases, respectively. In certain embodiments, more than one type of MMP may be incorporated into the matrix. By incorporating several types of MMPs into the tissue matrix, a variety of cellular processes can be regulated to further facilitate healing.

Additional enzymes can also be incorporated into the matrix along with the MMPs. These non-MMP enzymes may act to further facilitate tissue repair beyond that of adding only MMPs. In certain embodiments, additional enzymes include, but are not limited to, elastase and dispase. Elastase degrades elastin, another component found in extracellular matrices. Dispase hydrolyzes fibronectin and collagen IV, which are not generally degradable by MMP collagenases.

As discussed above, the particular MMP selected may be based on the matrikine desired as a result of extracellular matrix degradation. GHK (tripeptide glycyl-histidyl-lysine) (SEQ ID NO: 1), for example, is collagen-derived matrikine that is a potent activator of extracellular matrix synthesis and remodeling. CNYYSNS (heptapeptide cysteinyl-asparaginyl-tyrosyl-tyrosyl-seryl-asparaginyl-serine) (SEQ ID NO: 2) inhibits polymorphonuclear leukocyte activation and decreases the invasive capacities of cancer cells. In certain embodiments of the invention, desirable matrikines may include, but are not limited to GHK (SEQ ID NO: 1), CNYYSNS (SEQ ID NO: 2), VGPVG (SEQ ID NO: 3), VGVAPG (SEQ ID NO: 4), KKGHK (SEQ ID NO: 5), and DGGRYY (SEQ ID NO: 6).

A deactivating agent is used to inhibit MMP activity, thereby preventing degradation of the tissue matrix until the appropriate time. For example, with the proper deactivating agent, degradation of the tissue matrix can be inhibited until implantation into a subject. MMP inhibitors include endogenous inhibitors, such as TIMP-1, TIMP-2, TIMP-3, and TIMP-4, and synthetic inhibitors, such as phosphoramidon and bestatin. In certain embodiments, the MMP deactivation agent is a chelator. MMP activity is metal ion dependent. The chelating agent removes metal ions from the MMP active site, thereby deactivating the enzyme. Without being bound to theory, it is believed that the concentrations of metal ions naturally present in the body are able to replace ions that have been sequestered by the chelating agent, thereby automatically restoring MMP activity upon implantation into the body. Fluids in the body may also serve to wash away or dilute the deactivating agent, thereby restoring MMP activity. In certain embodiments, the chelating agent can include, but is not limited to EDTA, EGTA, and orthophenanthroline.

The deactivating agent also allows for regulation of tissue matrix degradation. Certain tissue products, such as small intestine submucosa, have been found to degrade rapidly when used in vivo, resulting in immediate and significant inflammation. This in turn, leads to poor remodeling of the tissue and subpar revascularization. Use of a deactivating agent allows for regulation of tissue degradation by modulating MMP activity, mitigating such undesirable effects.

A composition is prepared containing both the enzyme, such as the desired MMP, and the appropriate deactivating agent, such as EDTA, in order to incorporate the deactivated enzymes into the selected tissue matrix. In some embodiments, the composition containing both the enzyme and the deactivating agent is a solution. Any buffer can be used to prepare the solution so long as it permits the deactivation of the enzyme by the deactivating agent. In certain embodiments, the buffer comprises HEPES buffer. Other suitable buffers include PBS, TBS, MOPS, or any other biocompatible buffer known in the art and combinations thereof. The buffer can be at concentrations ranging from 1 to 100 mM (e.g., 1, 5, 10, 15, 20, 25, 30, 35, 40, 45, 50, 55, 60, 65, 70, 75, 80, 85, 90, 95 or 100 mM) in the solution.

The amount of enzyme in the solution can be adjusted to control the rate at which tissue matrix proteins are digested. In some embodiments, suitable concentrations of enzyme in solution range from 0.2 U/mL to 2.0 U/mL (e.g., 0.2, 0.5, 0.8, 1.0, 1.2, 1.5, 1.8, or 2 U/mL).

The amount of deactivating agent in the solution can also be adjusted to modulate the rate of protein digestion. In certain embodiments, suitable concentrations of chelating agent, for example EDTA, in solution range from 4 to 20 mM EDTA (e.g., 4, 6, 8, 10, 12, 14, 16, 18, 20 mM EDTA).

In some embodiments, the solution may also contain a salt. In certain embodiments, the amount of salt present in the solution serves to re-activate enzymatic activity by providing metallic ions. By controlling the relative amounts of salt, deactivating agent, and enzyme present in the solution, the rate of tissue degradation can be further modulated. Suitable salts include but are not limited to, calcium dihydrogen phosphate, calcium sulfate, calcium chloride, magnesium chloride, magnesium sulfate, manganese chloride, manganese sulfate. The concentration of salt in the solution can range from 2 to 10 mM (e.g., 2, 3, 4, 5, 6, 7, 8, 9, 10 mM) in the solution.

The composition containing the enzyme and the deactivating agent may also include protein stabilizers and radio-protectors. In certain embodiments, suitable protein stabilizers include glycerol, propylene glycol, ethylene glycol, mannitol, sucrose, trehalose or any combination thereof. In some embodiments, the concentration of protein stabilizers in solution may range from 5 to 250 mM (e.g., 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, and 250 mM). In certain embodiments, suitable radio-protectors include glycerol, propylene glycol, mannitol, trehalose or any combination thereof. The radio-protectors can range in concentration from 5 to 250 mM (e.g., 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, and 250 mM) in solution.

The tissue matrix is then contacted with the composition containing the enzyme and the deactivating agent. In certain embodiments, the tissue matrix is placed into the solution containing the enzyme and deactivating agent. In this instance, the enzymes have been deactivated prior to placing the tissue matrix into the solution. The deactivated enzymes are then incorporated into the tissue matrix as it incubates within the solution. In other embodiments, the tissue matrix, desired enzyme, and appropriate deactivating agent are placed into a suitable buffer at the same time and allowed to incubate.

In various embodiments, the disclosed methods can comprise additional processing of the tissue matrix. Such processing may include disinfection or sterilization of the tissue matrix. In some embodiments, the tissue matrix is sterilized with isopropyl alcohol (IPA) (e.g., at about 70% IPA).

The disclosed tissue matrix can be further treated to produce aseptic or sterile materials. Accordingly, in various embodiments, the matrices can be sterilized after preparation and in conjunction with packaging of the matrices. As used herein, a "sterilization process" can include any process that reduces bioburden in a sample, but need not render the sample absolutely sterile.

Certain exemplary processes include, but are not limited to, a gamma irradiation process, an e-beam irradiation process, ethylene oxide treatment, and propylene oxide treatment. Suitable sterilization processes include, but are not limited to, those described in, for example, U.S. Patent Publication No. 2006/0073592A1, to Sun et al.; U.S. Pat. No. 5,460,962 to Kemp; U.S. Patent Publication No. 2008/0171092A1, to Cook et al. In some embodiments, sterilization is performed in conjunction with packaging of the device, while in other embodiments, sterilization can occur after packaging.

After the matrices have been prepared by the disclosed methods, they may be stored for some time prior to implantation in or on a patient. In certain embodiments, the matrix may be packaged in a TYVEK® pouch for storage purposes. The matrix may also be stored in different states, for example, in a wet state or a freeze-dried state.

In some embodiments, the matrix is freeze-dried after preparation. Terminal sterilization by ionizing radiation after freeze-drying, however, can potentially damage freeze-dried tissue. To minimize this damage, the processed material can be packaged wet in moisture-permeable TYVEK® pouches first. The tissue is then irradiated in a wet state. After irradiation, the wet samples can be freeze-dried for storage.

The tissue matrix prepared by the methods described above can be used in various ways to facilitate tissue repair, regrowth, and regeneration. Accordingly, a method of treatment is provided. The method comprises selecting an anatomical site for treatment, selecting a collagen-based tissue matrix, wherein the matrix has been contacted with a composition containing an enzyme, wherein the composition containing an enzyme further contains a deactivating agent for deactivating activity of said enzyme, and implanting the collagen-based tissue matrix into the treatment site. "Into" as used herein, also means "onto." As discussed above, the enzyme activity of the disclosed tissue matrices has been inhibited prior to implantation in a subject, i.e., a human or animal patient. Once implanted, metal ions present in the subject are able to restore MMP activity suppressed by the chelating agent. With MMP activity restored, degradation of the tissue matrix commences, matrikines are released, and the healing process is facilitated.

An anatomical site for treatment, i.e., a treatment site, can be readily identified those skilled in the art. Examples include, but are not limited to, strained or torn tissue, or tissue having a gap, hole, or some other defect. Circumstances in which the disclosed tissue matrix can be used include the treatment of lumpectomies, pressure ulcers, diabetic foot ulcers, or periosteal bone defects. The tissue matrix may also be used in the treatment of facial defects, including wrinkles, skin loss, or skin atrophy. Additional uses may be readily identified by those skilled in the art.

The tissue matrices can be implanted in or on a variety of different anatomic sites. For example, tissue matrices can be implanted around breast implants; around or replacing vascular structures; around or replacing luminal structures (e.g., ureters, nerves, lymphatic tissues, gastrointestinal structures); on or replacing heart valves, pericardium, or other cardiac structures; in or on bony or cartilaginous materials (e.g., ears, noses, articular surfaces, around dental structures, or along any short or long bone); and/or surrounding, lining, supporting, or replacing any body cavity (e.g., bladder, stomach).

In certain embodiments, a bioactive substance is added to the tissue matrix which further facilitates tissue repair, regrowth, or regeneration. The bioactive substance can be added to the tissue matrix at any point prior to the implantation of the tissue matrix in a subject. For example, a bioactive substance can be added during preparation of the matrix but prior to its storage. In other embodiments, a bioactive substance may be added to the device after storage, but immediately prior to its implantation into a subject. Bioactive substances include, but are not limited to, antimicrobial agents, cytokines, growth factors, anti-inflammatory agents, steroids, and corticosteroids. In some embodiments, bioactive substances can include various types of tissue, for example, adipose tissue.

In some embodiments, the bioactive substance comprises cells that facilitate tissue repair, regrowth, or regeneration. In certain embodiments, the tissue matrices can be seeded with stem cells, such as mesenchymal stem cells, including embryonic stem cells and adult stem cells harvested from bone marrow, adipose tissue, and neuronal cells. In other embodiments, autologous stem cells may be used. In some embodiments, allogenic cells can be pre-seeded to the grafts and cultured in vitro and lysed before implantation.

Example 1: Preparation of Porcine Acellular Dermis Matrix (pADM)

Fresh porcine hides were collected and the hair removed. Dermal tissue 1.5 mm thick was obtained from the hides by removing the epidermis layer and subcutaneous fat (hypodermis) layer. The dermal tissue was then de-contaminated in PBS containing 50 units/ml penicillin, 1.25 µg/ml amphotercin B, and 50 µg/ml streptomycin for 24 hours at 37° C.

Further processing of the tissue was performed under aseptic conditions. The split dermis was decellularized by incubating the tissue in 10 mM HEPES buffer (pH 8.0) containing 2% sodium deoxycholate and 10 mM EDTA for 24 hours at ambient temperature with slight agitation. Decellularized porcine dermis was washed twice by incubating the tissue in 10 mM HEPES buffer containing 5 mM EDTA (pH 7.3) for 60 minutes per wash. The dermis was then incubated for 24 hours in HEPES buffer containing 2 mM $MgCl_2$, 2 mM $CaCl_2$, 1.0 mg/L DNAse, and 1 mg/L α-galactosidase to remove α-gal epitopes and other undesirable moieties. Cell debris and residual chemicals were removed by washing in PBS (pH 7.5) with gentle agitation 5 times over a 48-hour period. The density of the porcine acellular dermal matrix (pADM) was approximately 0.28 g dry tissue mass per cubicle centimeter. The pADM sheets had a final thickness of approximately 2.0 mm due to tissue swelling after processing. The pADM sheets were then frozen at −20° C. until further use.

Example 2: In Vitro Degradation of pADM by MMP-1

The pADM sheets were thawed in a 37° C. water bath. After thawing, tissue discs were prepared from the sheets using an 8-mm biopsy punch. Either one or three discs of pADM were then placed into 2 ml microfuge tubes. In vitro degradation of pADM by MMP-1 was performed by incubating the discs at 37° C. in 1.5 ml of 20 mM HEPES buffer (pH 7.4) containing 5 mM $CaCl_2$ and either 0.01, 0.1, 1.0, and 10 units/ml MMP-1. Sodium azide ($NaN_3$) was also added to the reaction solution at a final concentration of 0.01% as an anti-microbial.

The free amine content in the reaction solution was used to measure in vitro degradation of pADM resulting from MMP-1 activity. After 16 hours, a 25 µL aliquot of the reaction solution was removed to a 2 ml microfuge tube and subsequently diluted with 475 µL 100 mM sodium bicarbonate solution containing 5 mM EDTA. 250 µl of 0.05% picryl sulfonic acid (PSA) was then added and mixed into the sample, which was then incubated for 45 minutes at 37° C. After incubation, 250 µl 10% SDS and 125 µL 1N HCl were added into each sample.

Figure 2:
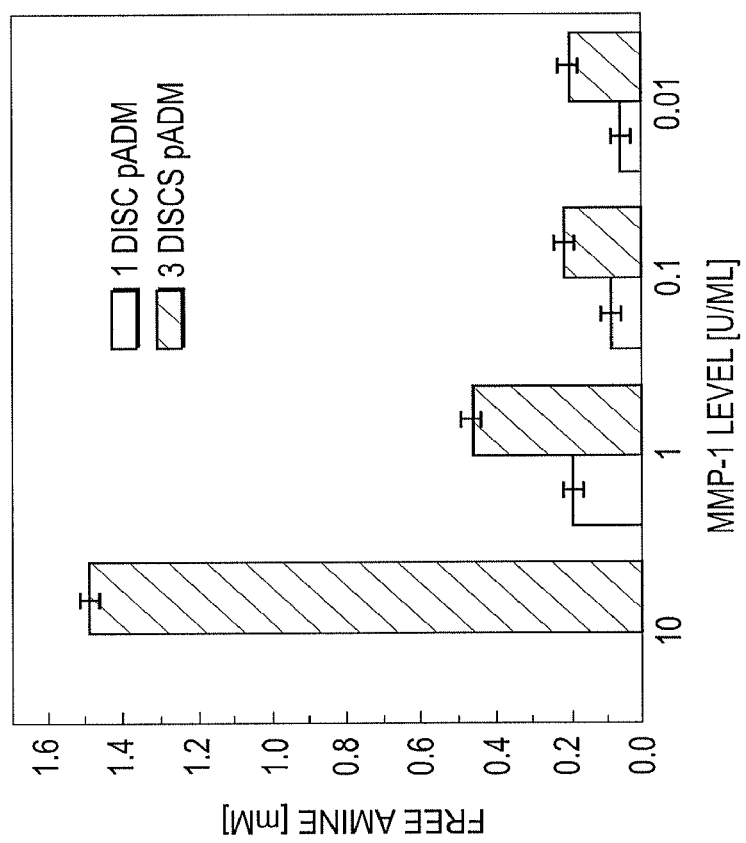
FIG. 2 is a chart showing the concentration of free amines released due to tissue matrix degradation, according to certain embodiments and described in Example 2.

Free amine content was measured at 345 nm by spectrophotometer, using glycine as a standard. Experiments were repeated in triplicate with results recorded as mean±standard deviation. The amount of free amines released from the pADM at varying concentrations of MMP-1 is shown in FIG. 2. Even at low MMP-1 concentrations approaching physiological conditions (0.01 and 0.1 units/ml), a considerable increase of free amines was detected in the reaction solution, demonstrating the suitability of the assay for in vitro testing.

Figures 3A, 3B:
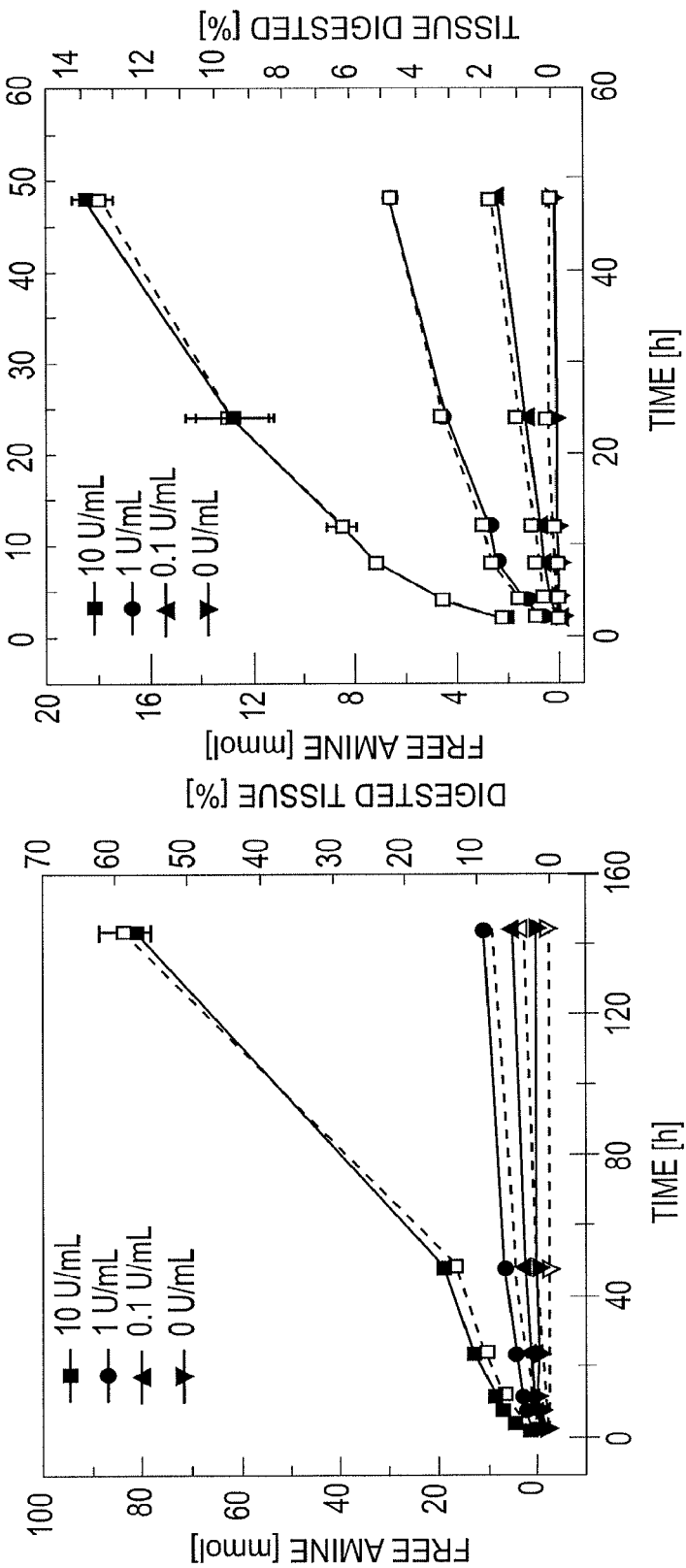
FIGS. 3A and 3B are charts showing changes in free amine concentration due to tissue matrix degradation over two separate time periods, according to certain embodiments and described in Example 2.

The kinetics of pADM degradation by MMP-1 over a 144 hour period is shown in FIG. 3A. As determined by the release of free amines, no degradation of pADM was observed with the control group (0 units/ml MMP-1). As the concentration of MMP-1 increased, however, the rate of pADM degradation also increased proportionately. The assay continued to demonstrate significant sensitivity. At an MMP-1 concentration of 0.1 units/ml, for example, a small but steady increase in the content of free amines was detected, which corresponded to approximately 3% degradation of pADM. In FIG. 3B, degradation kinetics over a 44 hour period is shown with similar results.

Example 3: Deactivation of MMP-1

EDTA was used as a "reversible switch" to control MMP-1 activity within the pADM. As a chelator, EDTA can sequester calcium and magnesium ions within the pADM, thereby inhibiting MMP-1 activity. Tissue discs were incubated at 37° C. in 1.5 ml of reaction solution (pH 7.4) containing 20 mM HEPES, 5 mM $CaCl_2$, and 10 units/ml MMP-1. EDTA was also added into the reaction solution to stop degradation. After 72 hours of incubation, the content of free amines in the reaction solution was measured using the PSA assay described in Example 2.

Figure 4A:
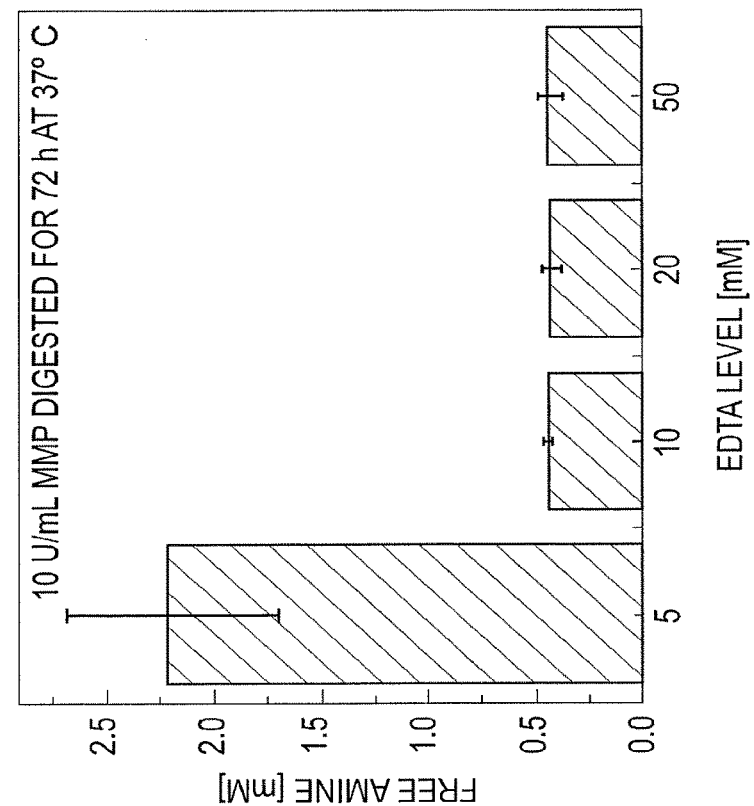
FIGS. 4A and 4B are charts showing the inhibition of MMP-1 activity by EDTA in a fixed concentration of MMP-1 and in varying concentrations of MMP-1 respectively, according to certain embodiments and described in Example 3.
Figure 4B:
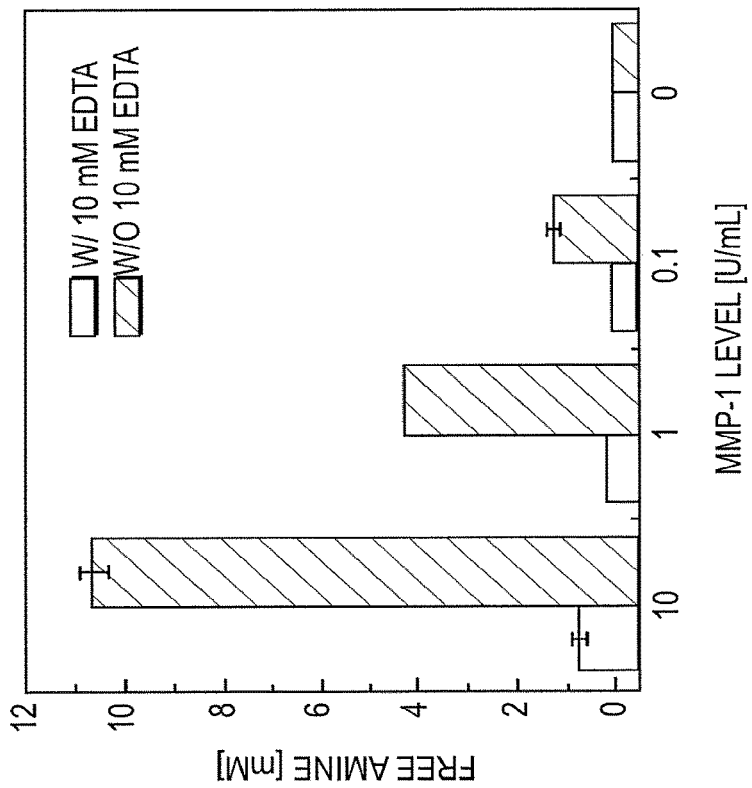

The addition of EDTA into the reaction solution resulted in suppression of MMP-1 activity. As shown in FIG. 4A, no further MMP-1 activity was detected when the concentration of EDTA was higher than the concentration of $CaCl_2$. The effect of EDTA (10 mM) on MMP-1 activity was also tested at other concentrations of MMP-1. As shown in FIG. 4B, 10 mM EDTA inhibited MMP-1 activity at MMP-1 concentrations of 1.0 units/ml and lower.

Example 4: Reactivation of Deactivated MMP-1

Figure 5:
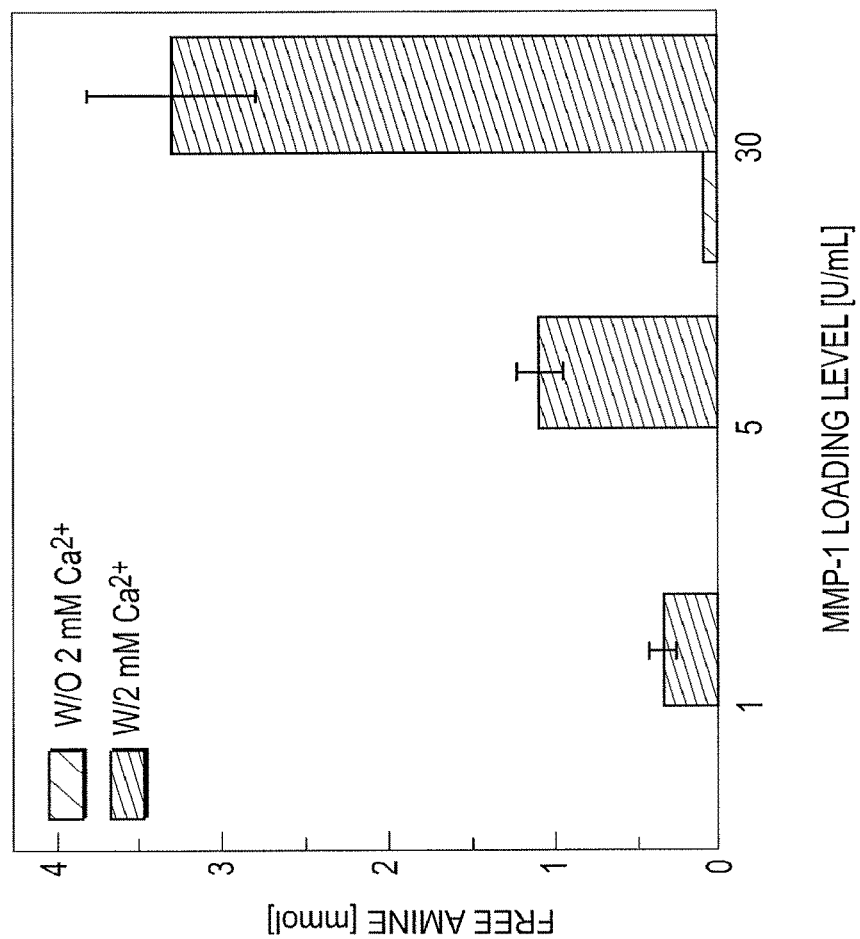
FIG. 5 is a chart showing the restoration of suppressed MMP-1 activity by the addition of calcium ions, according to certain embodiments and described in Example 4.

Samples of pADM matrix were loaded with MMP-1, prepared at concentrations of 1, 5, or 30 units/ml in HEPES buffer (pH 7.4). EDTA was added to each sample at a final concentration of 2.0 mM to deactivate MMP-1. The samples were then incubated at 4° C. overnight to allow MMP-1 to infiltrate into the tissue matrix. The activity of MMP-1 in the tissue discs was then measured at 37° C. in fresh 20 mM HEPES solution (pH 7.4) with and without 2 mM $CaCl_2$. As shown in FIG. 5, the addition of calcium ions restored suppressed MMP-1 activity, indicated by the increased content of free amines in HEPES solution.

Example 5: Preparation of Human Acellular Dermis Matrix (hADM)

Human donor skin was obtained from a certified U.S. tissue bank with the appropriate consent. Procured skin was shipped to the testing site in RPMI 1640 solution containing antibiotics (penicillin and streptomycin) in the presence of ice. Upon arrival, the skin was cryopreserved at −80° C.

The skin tissue was processed under aseptic conditions. Frozen skin was thawed at 37° C., removing all visible traces of ice. Epidermis was separated from dermis by incubating skin tissue in 1.0 M sodium chloride with 0.5% (w/v) TRITON X-100™ for 24 hours at room temperature. Cellular elements in the dermis were removed by incubating the dermis material in 10 mM HEPES buffer (pH 8.0) containing 2% (w/v) sodium deoxycholate and 10 mM EDTA for 18 hours, and then by washing the material in PBS (pH 7.5) with gentle agitation 5 times over a 48 hour period. The resulting sheets of human acellular dermis matrix ("hADM") had a density of approximately 0.15 g dry tissue mass per cubicle centimeter and were approximately 2.0 mm thick. The hADM sheets were subsequently frozen at −20° C. until use.

Example 6: In Vitro Degradation of hADM by MMP-1

Figure 6A:
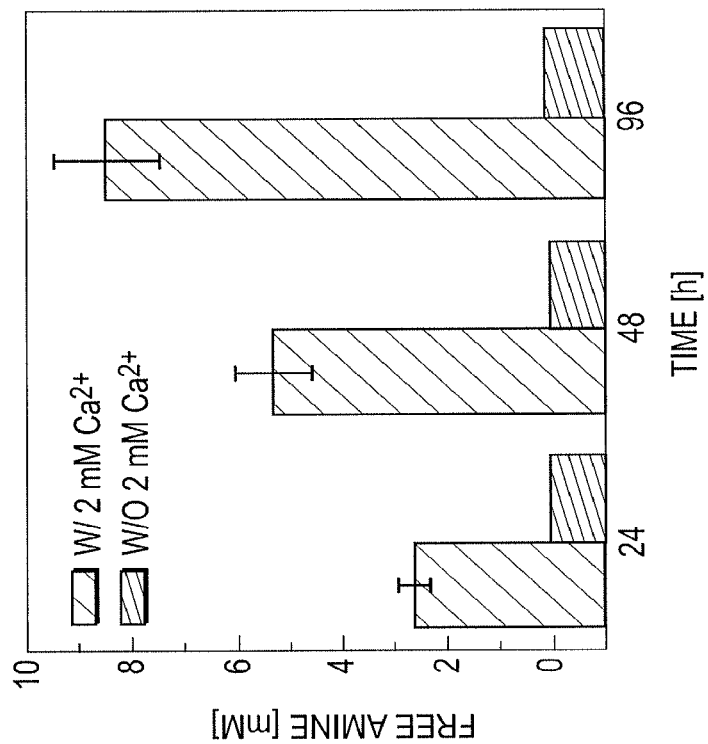
FIGS. 6A and 6B are charts showing the concentration of free amines released from human acellular dermis matrix (hADM) after MMP-1 induced degradation and the restoration of MMP-1 activity respectively, according to certain embodiments and described in Example 6.

The hADM sheets were thawed in a 37° C. water bath. After thawing, tissue discs were prepared from the sheets using an 8-mm biopsy punch and incubated in 1.5 ml reaction solution (20 mM HEPES, 5 mM $CaCl_2$, pH 7.4). Test samples were prepared by adding MMP-1 to the reaction solutions at final concentrations of 0, 0.1, and 1.0 units/ml. After incubating the samples at 37° C. for 40 hours, the content of free amines in the samples was measured using the previously described PSA assay. The amount of free amines that were released from hADM is shown in FIG. 6A. No free amine was detected in the control sample solution (0 units/ml MMP-1). An increase in the amount of free amines was observed at higher concentrations of MMP-1.

Figure 6B:
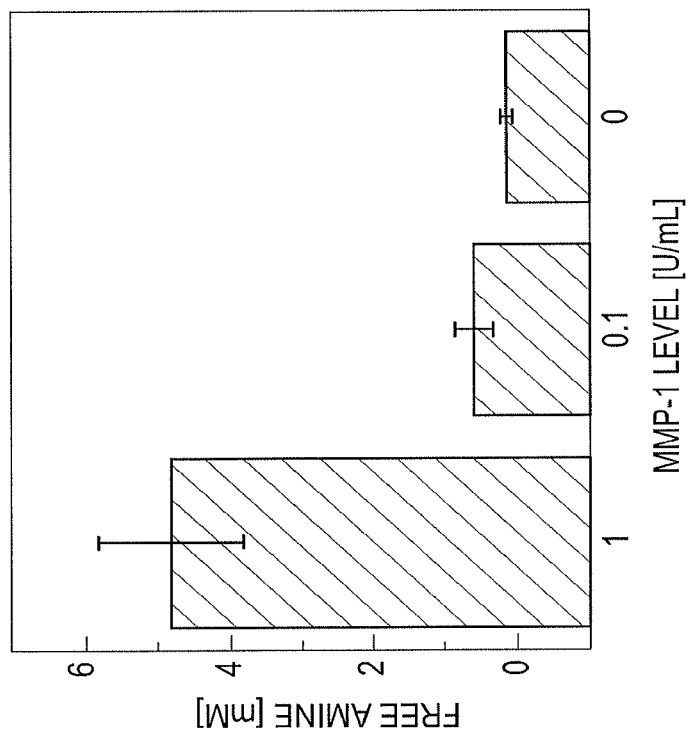

For the reactivation study, tissue discs of hADM were incubated in 2.0 ml HEPES buffer containing 5 units/ml MMP-1 and 2 mM EDTA at 4° C. overnight. After incubation, the hADM discs containing inactivated MMP-1 were divided into two groups. In the first group, tissue discs were placed in 1.5 ml 20 mM HEPES (pH 7.4) with 2 mM $CaCl_2$. In the second group, tissue discs were placed in 1.5 ml 20 mM HEPES (pH 7.4) without $CaCl_2$. Vials containing the samples were incubated at 37° C. with gentle agitation. The free amine concentrations in sample solutions were measured after 24, 48, and 96 hours. As shown in FIG. 6B, MMP-1 activity was restored with the addition of 2 mM $CaCl_2$ and increased in a time-dependent manner.

Example 7: Effect of MMP-1 Treatment on Mechanical Properties of pADM

A pADM sheet prepared according to Example 1 was cut into 0.8 cm×6.0 cm strips with a scalpel. To reduce experimental error, all the tissue strips were cut in the same direction. The strips were grouped into sets of three and placed into individual 15 mL conical tubes. In vitro MMP-1 treatment was performed at 37° C. in 20 mM HEPES buffer (pH 7.4) containing 5 mM $CaCl_2$. The pADM strips were immersed in 12 mL of the HEPES solution with 1 unit/ml MMP-1. Sodium azide ($NaN_3$) was added to the solution at a final concentration of 0.01% as an antimicrobial. MMP-1 treatment was terminated by transferring the pADM strips into 20 mM HEPES buffer containing 10 mM EDTA at 48 hours, 96 hours, and 144 hours, respectively. Upon removing the strips, the buffer was collected and free amine levels were determined using the assay procedure described in Example 2. Tensile tests were performed on the pADM tissue strips under the following test conditions: 1 KN load cell, 4 mm gauge length, and crosshead speed of 1.0 mm/min.

Figures 7A, 7B:
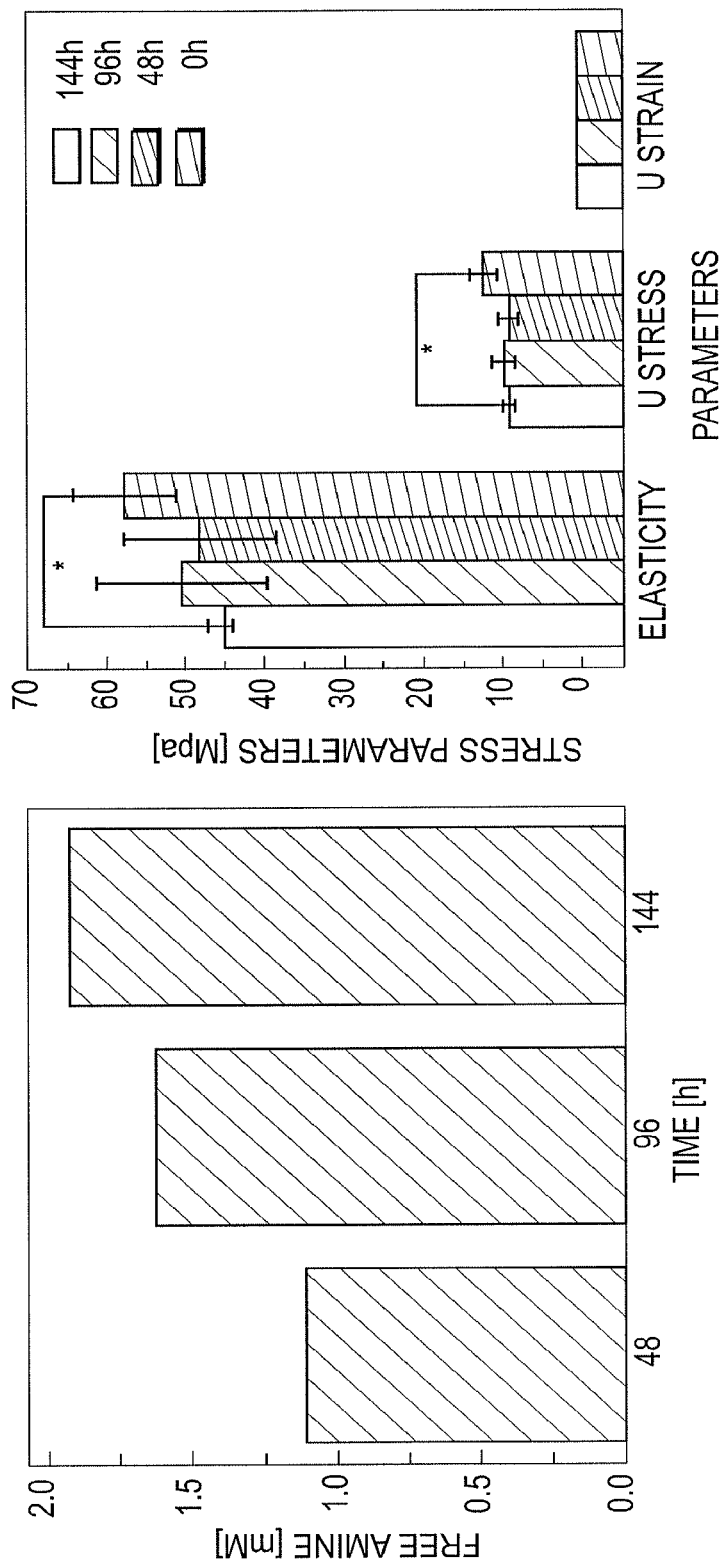
FIGS. 7A and 7B are charts showing the concentration of free amines released from porcine acellular dermal matrix (pADM) after MMP-1 induced degradation and the effect of MMP-1 on pADM mechanical properties, respectively, according to certain embodiments and described in Example 7.

As shown in FIG. 7A, the amount of free amine in solution increased with the duration of MMP-1 treatment, demonstrating the continuous degradation of pADM over time. As shown in FIG. 7B, the mechanical properties of treated pADM did not change upon degradation of the pADM. After a 96 hour treatment with 1 unit/ml MMP-1, no significant change was observed for the three parameters measured: elasticity, ultimate stress, and ultimate strain. When treatment time increased to 144 hours, however, a significant drop in elasticity and ultimate stress was found in comparison to pADM without MMP-1 treatment. As shown in FIG. 7B, no significant change in ultimate strain was observed upon MMP-1 treatment as a result of time.

Figure 8:
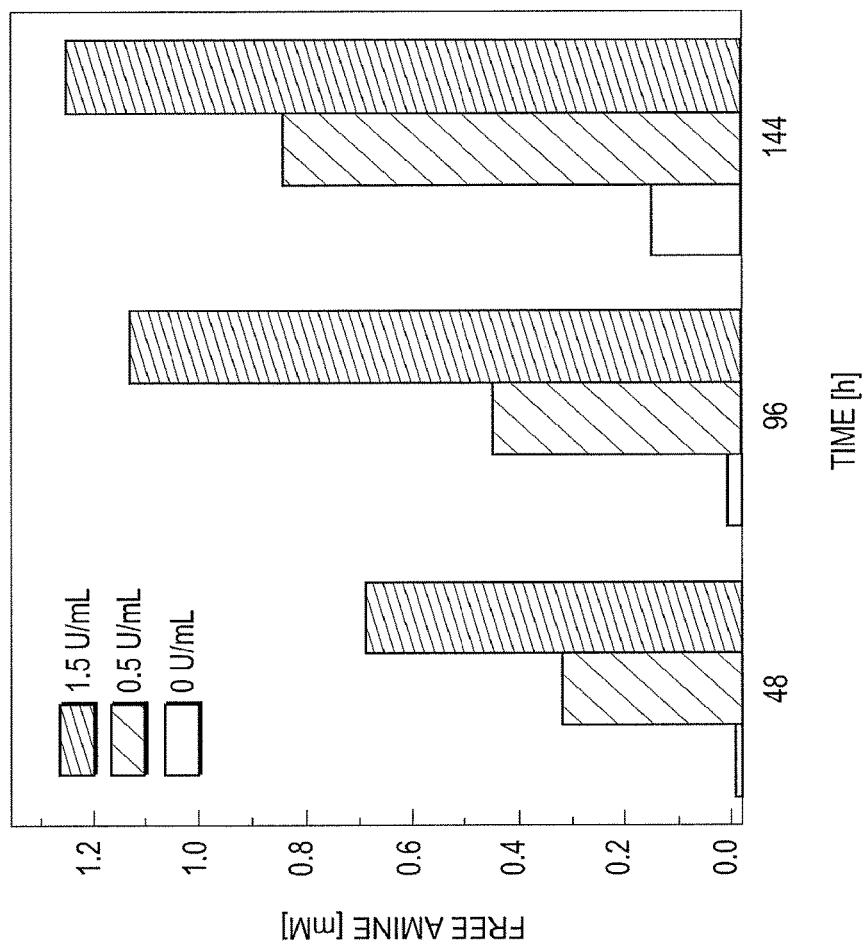
FIG. 8 is a chart showing the concentration of free amines released as a function of time after MMP-1 treatment, according to certain embodiments and described in Example 8.

Example 8: Effect of MMP-1 Treatment on pADM Thermal Stability pADM discs were prepared using a 5.0 mm biopsy punch. The discs were then incubated in sets of three in 1.5 ml reaction buffer (20 mM HEPES, 5 mM $CaCl_2$, 0.01 $NaN_3$, pH 7.4) containing either 0, 0.5, or 1.5 units/ml MMP-1. At 0, 48, 96, and 144 hours of incubation, the tissue discs in one tube from each concentration level were transferred to 20 mM HEPES buffer containing 10 mM EDTA to quench MMP-1 activity. The remaining reaction buffer was used for free amine determination as described in Example 2. FIG. 8 shows pADM degradation based on free amine release upon addition of MMP-1 at concentrations of 1.5 and 0.5 units/ml. The release of free amines increased proportionately with treatment time, indicating that enzyme-mediated degradation of pADM is a steady process. Very limited amounts of free amine was detected in the group without MMP-1.

The effect of MMP-1 degradation on tissue matrix stability was investigated using a differential scanning calorimeter ("DSC") (Q100, TA Instruments, New Castle, Del.). The tissue discs described above were equilibrated in PBS for at least 3 hours. The tissue discs were then blotted dry with Kimwipe® paper. Next, the blot-dried tissue discs were hermetically sealed in an aluminum DSC crucible. All samples were scanned at a heating rate of 2° C. min-1 from 2° C. to 120° C. with nitrogen as the purge gas. After DSC measurement, small holes were created on the lids of the sealed crucibles, which were then dried between 105° C. and 110° C. under vacuum overnight. The dry mass of the samples was then measured based on the crucible mass. Thermograms were analyzed using Universal Analysis to determine the onset temperature ($T_d$) and enthalpy of collagen denaturation. As shown in FIG. 9A, no significant difference was observed from the DSC thermograms obtained from pADM treated with 1.5 units/ml MMP-1 for the different time periods. Neither the denature onset temperature nor the enthalpy for collagen denaturation demonstrated substantial change. As shown in FIG. 9B, no significant differences were observed using DSC for pADM treated with different concentrations of MMP-1 at 144 hours. These results indicate that the degradation of pADM mediated by MMP-1 is more likely to be a general degradation of collagen fibers rather than specific components of the tissue matrix.

Example 9: Degradation of pADM Using MMP-3 and MMP-9

Recombinant MMP-3 and MMP-9 (Sigma, USA) were first incubated with 1 mM 4 aminophenylmercuric acetate ("APMA") for 4 hours at 37° C. to activate the MMPs. 8 mm pADM discs were again used to test MMP-mediated degradation. The tissue discs were incubated in groups of three in 1.5 ml reaction buffer (20 mM HEPES, 5 mM $CaCl_2$, 0.01% $NaN_3$, pH 7.4) containing either 0.5 µg/ml MMP-3 or MMP-9. After 24 and 48 hours of incubation at 37° C., 25 µl aliquots were taken from each tube for determine levels of free amine resulting from MMP-3 or MMP-9 mediated degradation. Free amine results for both 24 and 48-hour incubation periods show that no detectable free amine was found in either MMP-3 or MMP-9 reaction buffers. Neither MMP-3 nor MMP-9 digest type I collagen, which is the primary component of the pADM. Therefore, it is expected no substantial increase in free amine was observed after treatment with these enzymes.

Example 10: Change in Thermal Stability of pADM after Subcutaneous Implantation

Figures 10A, 10B:
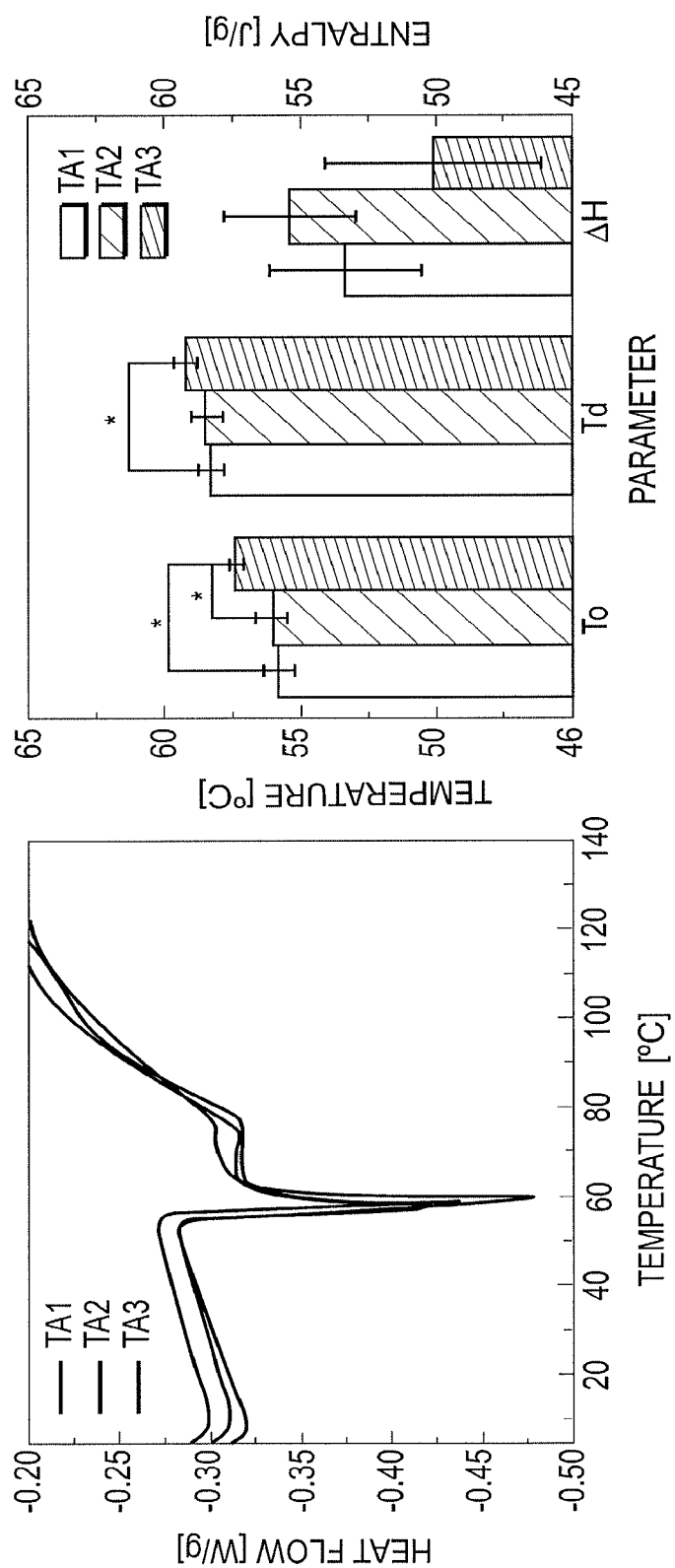
FIGS. 10A and 10B are charts showing the effects of subcutaneous implantation on tissue matrices, according to certain embodiments and described in Example 10.

Three preparations of pADM were made and implanted subcutaneously into rats: TA1, firm tissue derived from pig spinal region; TA2, firm tissue derived from pig spinal region that was dried and subsequently rehydrated; and TA3, pliant tissue derived from pig belly. After 20 days, the preparations of pADM were harvested and the animal tissue surrounding the pADM was carefully cleaned using forceps. 5 mm discs were then obtained from the explanted pADM using a biopsy punch and blotted dry with Kimwipe® paper. Once dried, the tissue discs were hermetically sealed in an aluminum DSC crucible. DSC measurements were run for all explants using the same settings described in Example 8. Thermograms were analyzed using Universal Analysis to determine the onset temperature ($T_o$), denaturation temperature ($T_d$) and enthalpy of collagen denaturation ($\Delta H$). The subsequent thermal analysis indicated that no significant change occurred based on any change in composition. It is believed that the majority of pADM was not remodeled in rats because the DSC curves showed only slight differences between the different groups, as shown in FIG. 10A. In addition, FIG. 10B shows that although the differences of onset temperature and denaturation temperature between the three groups were mild overall, the onset and denaturation temperatures were still statistically higher for TA3. No significant differences were observed between the three groups with respect to enthalpy. Taken together, this indicates that tissue remodeling can be very slow in vivo, presenting a need for rapid remodeling via enzyme activation.

What is claimed is:

1. A method of treatment comprising:
   selecting an anatomical site for treatment;
   selecting a collagen-based acellular tissue matrix, wherein the matrix has been contacted with a composition containing at least one protease, wherein the protease consists essentially of at least one of MMP-1, MMP-3, or MMP-9, wherein the protease can cleave one or more matrikines from the tissue matrix, and wherein the composition further contains a deactivating agent comprising one or more chelators for reducing the activity of the at least one protease by binding metal ions needed for activity of the at least one protease; and
   implanting the collagen-based acellular tissue matrix into the anatomic site.

2. The method of claim 1, wherein the acellular tissue matrix comprises an acellular dermal matrix.

3. The method of claim 2, wherein the acellular tissue matrix comprises an acellular porcine dermal matrix.

4. The method of claim 1, wherein the protease is a matrix metalloproteinase (MMP).

5. The method of claim 1, wherein the at least one protease is in a solution.

6. The method of claim 1, wherein the composition further contains at least one of an elastase or a dispase.

7. The method of claim 1, wherein the chelating agent comprises ethylenediaminetetraacetic acid (EDTA), ethylene glycol tetraacetic acid (EGTA), or orthophenanthroline.

8. The method of claim 1, wherein the chelating agent regulates the degradation of the tissue matrix by modulating protease activity.

9. The method of claim 1, further comprising exposing the acellular tissue matrix to a disinfectant.

10. The method of claim 9, wherein the disinfectant is isopropyl alcohol.

11. The method of claim 1, further comprising sterilizing the acellular tissue matrix.

12. The method of claim 11, wherein sterilizing the acellular tissue matrix comprises application of ethylene oxide, propylene, gamma irradiation, or e-beam irradiation.

13. The method of claim 1, further comprising lyophilizing the acellular tissue matrix.

14. The method of claim 1, further comprising storing the acellular tissue matrix in a hydrated state prior to implanting the acellular tissue matrix into the anatomical site.

15. The method of claim 1, wherein the composition further contains a bioactive substance.

16. The method of claim 15, wherein the bioactive substance comprises an antibacterial agent, a cytokine, a growth factor, non-collagenous tissue, or cells.

17. The method of claim 1, wherein the activity of the protease is restored automatically upon implantation into a subject.

18. The method of claim 17, wherein the restoration of protease activity results in the release of matrikines from the tissue matrix.

19. The method of claim 1, wherein the matrikines comprise GHK (SEQ ID NO: 1), CNYYSNS (SEQ ID NO: 2), VGPVG (SEQ ID NO: 3), VGVAPG (SEQ ID NO: 4), KKGHK (SEQ ID NO: 5), or DGGRYY (SEQ ID NO: 6).

20. The method of claim 1, wherein the chelator is present in the composition at a concentration between 4 mM and 20 mM.

* * * * *